(12) United States Patent
Truckai et al.

(10) Patent No.: US 9,247,983 B2
(45) Date of Patent: Feb. 2, 2016

(54) MEDICAL INSTRUMENT AND METHOD OF USE

(71) Applicants: Csaba Truckai, Saratoga, CA (US);
Aaron Germain, Campbell, CA (US);
John H. Shadduck, Menlo Park, CA (US)

(72) Inventors: Csaba Truckai, Saratoga, CA (US);
Aaron Germain, Campbell, CA (US);
John H. Shadduck, Menlo Park, CA (US)

(73) Assignee: ARQOS Surgical, Inc., Cupertino, CA (US)

( * ) Notice: Subject to any disclaimer, the term of this patent is extended or adjusted under 35 U.S.C. 154(b) by 279 days.

(21) Appl. No.: 13/676,249

(22) Filed: Nov. 14, 2012

(65) Prior Publication Data
US 2013/0317492 A1 Nov. 28, 2013

Related U.S. Application Data

(60) Provisional application No. 61/559,519, filed on Nov. 14, 2011.

(51) Int. Cl.
*A61B 18/18* (2006.01)
*A61B 18/08* (2006.01)
*A61B 18/14* (2006.01)
*A61B 18/00* (2006.01)

(52) U.S. Cl.
CPC .............. *A61B 18/08* (2013.01); *A61B 18/085* (2013.01); *A61B 18/1445* (2013.01); *A61B 2018/00589* (2013.01); *A61B 2018/00601* (2013.01); *A61B 2018/146* (2013.01)

(58) Field of Classification Search
USPC ............................................ 606/41; 607/37
See application file for complete search history.

(56) References Cited

U.S. PATENT DOCUMENTS

| 2,513,564 | A | 7/1950 | Ingwersen |
| 2,514,545 | A | 7/1950 | Ingwersen |
| 2,625,625 | A | 1/1953 | Ingwersen |
| 2,689,895 | A | 9/1954 | Ingwersen |
| 3,611,023 | A | 10/1971 | Souza, Jr. et al. |
| 3,838,242 | A | 9/1974 | Goucher |
| 3,848,211 | A | 11/1974 | Russell |
| 3,868,614 | A | 2/1975 | Riendeau |
| 3,903,891 | A | 9/1975 | Brayshaw |
| 4,060,088 | A | 11/1977 | Morrison, Jr. et al. |

(Continued)

FOREIGN PATENT DOCUMENTS

| EP | 1034747 A1 | 9/2000 |
| WO | WO 00/53112 A2 | 9/2000 |

(Continued)

OTHER PUBLICATIONS

U.S. Appl. No. 13/287,315, filed Nov. 2, 2011, Germain et al.

(Continued)

*Primary Examiner* — Nicole F Lavert
(74) *Attorney, Agent, or Firm* — Wilson Sonsini Goodrich & Rosati

(57) ABSTRACT

A medical for removing tissue from a patient includes an elongated probe with a working end. A pair of jaws is provided at the working end. The jaws may be closed for cutting and treatment of the tissue. Cutting may be effective through a sharpened cutting blade, and RF cutting blade, and similar cutting edges. The tissue may be remodeled using heat generated from passive heating elements on the jaws, active heating elements on the jaws, a PTCR heating element carried by the jaws, or resistive heaters on the jaws.

13 Claims, 4 Drawing Sheets

(56) References Cited

U.S. PATENT DOCUMENTS

| | | |
|---|---|---|
| 4,272,687 A | 6/1981 | Borkan |
| 4,781,175 A | 11/1988 | McGreevy et al. |
| 4,977,346 A | 12/1990 | Gibson et al. |
| 5,012,495 A | 4/1991 | Munroe et al. |
| 5,122,138 A | 6/1992 | Manwaring |
| 5,207,675 A | 5/1993 | Canady |
| 5,256,138 A | 10/1993 | Burek et al. |
| 5,281,217 A | 1/1994 | Edwards et al. |
| 5,449,356 A | 9/1995 | Walbrink et al. |
| 5,669,907 A | 9/1997 | Platt, Jr. et al. |
| 5,683,366 A | 11/1997 | Eggers et al. |
| 5,720,745 A | 2/1998 | Farin et al. |
| 5,776,092 A | 7/1998 | Farin et al. |
| 5,779,715 A * | 7/1998 | Tu .................... 606/108 |
| 5,849,010 A | 12/1998 | Wurzer et al. |
| 5,873,855 A | 2/1999 | Eggers et al. |
| 5,888,198 A | 3/1999 | Eggers et al. |
| 5,891,095 A | 4/1999 | Eggers et al. |
| 5,964,752 A | 10/1999 | Stone |
| 5,989,248 A | 11/1999 | Tu et al. |
| 6,013,075 A | 1/2000 | Avramenko et al. |
| 6,013,076 A | 1/2000 | Goble et al. |
| 6,024,733 A | 2/2000 | Eggers et al. |
| 6,032,674 A | 3/2000 | Eggers et al. |
| 6,039,736 A | 3/2000 | Platt, Jr. |
| 6,056,747 A | 5/2000 | Saadat et al. |
| 6,066,134 A | 5/2000 | Eggers et al. |
| 6,099,523 A | 8/2000 | Kim et al. |
| 6,142,992 A | 11/2000 | Cheng et al. |
| 6,149,620 A | 11/2000 | Baker et al. |
| 6,159,208 A | 12/2000 | Hovda et al. |
| 6,225,883 B1 | 5/2001 | Wellner et al. |
| 6,235,020 B1 | 5/2001 | Cheng et al. |
| 6,238,391 B1 | 5/2001 | Olsen et al. |
| 6,296,636 B1 | 10/2001 | Cheng et al. |
| 6,348,051 B1 | 2/2002 | Farin et al. |
| 6,394,956 B1 | 5/2002 | Chandrasekaran et al. |
| 6,413,256 B1 | 7/2002 | Truckai et al. |
| 6,419,674 B1 | 7/2002 | Bowser et al. |
| 6,443,948 B1 | 9/2002 | Suslov |
| 6,475,215 B1 | 11/2002 | Tanrisever |
| 6,538,549 B1 | 3/2003 | Renne et al. |
| 6,579,289 B2 | 6/2003 | Schnitzler |
| 6,632,220 B1 | 10/2003 | Eggers et al. |
| 6,669,694 B2 | 12/2003 | Shadduck |
| 6,720,856 B1 | 4/2004 | Pellon et al. |
| 6,780,178 B2 | 8/2004 | Palanker et al. |
| 6,821,275 B2 | 11/2004 | Truckai et al. |
| 6,837,884 B2 | 1/2005 | Woloszko |
| 6,890,332 B2 | 5/2005 | Truckai et al. |
| 6,902,564 B2 | 6/2005 | Morgan et al. |
| 7,087,054 B2 | 8/2006 | Truckai et al. |
| 7,220,261 B2 | 5/2007 | Truckai et al. |
| 7,309,849 B2 | 12/2007 | Truckai et al. |
| 7,549,989 B2 | 6/2009 | Morgan et al. |
| 7,713,269 B2 | 5/2010 | Auge, II et al. |
| 7,744,595 B2 | 6/2010 | Truckai et al. |
| 7,771,422 B2 | 8/2010 | Auge, II et al. |
| 7,819,861 B2 | 10/2010 | Auge, II et al. |
| 7,819,864 B2 | 10/2010 | Morgan et al. |
| 7,955,331 B2 | 6/2011 | Truckai et al. |
| 8,016,823 B2 | 9/2011 | Shadduck |
| 8,075,555 B2 | 12/2011 | Truckai et al. |
| 8,192,424 B2 | 6/2012 | Woloszko |
| 8,192,428 B2 | 6/2012 | Truckai et al. |
| 8,221,404 B2 | 7/2012 | Truckai |
| 8,323,280 B2 | 12/2012 | Germain et al. |
| 8,333,763 B2 | 12/2012 | Truckai et al. |
| 2003/0014051 A1 | 1/2003 | Woloszko |
| 2003/0125727 A1 | 7/2003 | Truckai et al. |
| 2004/0044341 A1 | 3/2004 | Truckai et al. |
| 2005/0075630 A1 | 4/2005 | Truckai et al. |
| 2005/0228372 A1 | 10/2005 | Truckai et al. |
| 2006/0058782 A1 | 3/2006 | Truckai et al. |
| 2006/0224154 A1 | 10/2006 | Shadduck et al. |
| 2007/0213704 A1 | 9/2007 | Truckai et al. |
| 2009/0076498 A1 | 3/2009 | Saadat et al. |
| 2009/0270849 A1 | 10/2009 | Truckai et al. |
| 2009/0299365 A1 * | 12/2009 | Stewart et al. ............ 606/41 |
| 2010/0100091 A1 | 4/2010 | Truckai |
| 2010/0305565 A1 | 12/2010 | Truckai et al. |
| 2012/0245580 A1 | 9/2012 | Germain et al. |
| 2012/0330292 A1 | 12/2012 | Shadduck et al. |
| 2014/0163664 A1 * | 6/2014 | Goldsmith ............ 623/1.11 |

FOREIGN PATENT DOCUMENTS

| | | |
|---|---|---|
| WO | WO 00/62685 A1 | 10/2000 |
| WO | WO 00/53112 A3 | 12/2000 |

OTHER PUBLICATIONS

U.S. Appl. No. 13/369,983, filed Feb. 9, 2012, Truckai et al.
U.S. Appl. No. 13/664,232, filed Oct. 30, 2012, Germain et al.
U.S. Appl. No. 13/680,972, filed Nov. 19, 2012, Truckai et al.
European search report dated Nov. 2, 2009 for EP Application No. 01967968.7.
Kim, et al. Optical feedbacksignal for ultra short pulse ablation of tissue. Appl. Surface Sci. 1998; 127-129:857-862.
International search report dated Jan. 14, 2002 for PCT/US2001/025409.
International search report and written opinion dated May 23, 2012 for PCT/US2012/023390.
Tucker et al. Histologic characteristics of electrosurgical injuries. J. Am. Assoc. Gyneco. Laproscopy. 1997; 4(2):857-862.

* cited by examiner

MEDICAL INSTRUMENT AND METHOD OF USE

CROSS-REFERENCE TO RELATED APPLICATIONS

This application claims the benefit of Provisional Application No. 61/559,519, filed Nov. 14, 2011, the entire contents of which are incorporated herein by reference.

BACKGROUND OF THE INVENTION

1. Field of the Invention

This invention relates to medical devices and techniques and more particularly relates to instruments that are adapted to transect joint tissue and electrosurgically remodel the cut edges of remaining tissue.

SUMMARY OF THE INVENTION

The object of the present invention is to provide an instrument working end capable of (i) transecting tissue and (ii) providing a controlled application of heat for remodeling the tissue edges that remain following the transecting step.

Additional objects and advantages of the invention will be apparent from the following description, the accompanying drawings and the appended claims.

In a first aspect of the present invention, methods for treating tissue, such as cartilage and other joint tissues, comprise clamping a selected tissue volume between a first jaw and second jaw. While the tissue is or remains clamped between the jaws, it is cut with a first cutting element disposed on at least one jaw and remodeled with a remodeling element disposed on at least one jaw. The cutting and remodeling elements may be on both jaws and may comprise different components disposed on either or both jaws. By "remodeling," it is meant that the tissue will be heated in order to denature the collagen therein and will be reshaped or reformed in a manner which provides physiologic benefit when the treatment is completed. In exemplary embodiments, the tissue will be remodeled to receive a tapered edge which can have physiologic benefits, particularly in treatment of cartilage and other joint tissues.

In a second aspect, the present invention comprises a medical device for resecting and remodeling tissue. In particular, the device comprises an elongate probe with a working end and first and second "openable-closable" jaws operably connected to the working end of the probe. At least one of two jaws will have a first surface portion carrying a tissue cutting element. At least one of the two jaws, which may be the same or different than the jaw carrying the tissue cutting element, will carry a heat emitter for applying thermal energy for remodeling tissue.

In both the method and device aspects of the present invention, the tissue cutting element may comprise a sharp edge disposed about a perimeter of at least one jaw, such as a cutting blade which shears against an edge of the opposed jaw. Alternatively, the cutting element may comprise a radio frequency (RF) electrode which is carried on or over a perimeter of at least one jaw.

In both the method and device aspects of the present invention, the remodeling will be accomplished by application of heat to the tissue, preferably while the tissue remains clamped between the jaws. The heating may be provided by Joule heating, passive conductive heating, or both. Alternatively, the heating may result from passing RF current between first and second electrodes carried by one or both of the jaws where the RF current results in heating of the tissue. In a third example, the tissue heating may be achieved by passing current through a positive temperature coefficient of resistance (PTCR) material which results in a temperature-controlled heating depending on the nature of material.

In specific embodiments, the heat emitter may comprise a first tapered surface on one jaw and a second tapered surface on the other jaw. The tapered surfaces diverge in a laterally outward direction from the jaws so that the tissue, when clamped between the closed jaws, is reformed into an inward tapered tissue margin after the tissue was cut and heated by the device.

In still further specific embodiments of the present invention, the device may include means for removing the cut tissue from the treatment area. For example, the probe may be configured to provide further transport of the cut tissue in a proximal direction, for example within a channel extending through the probe. Optionally, a negative pressure source may be provided in order to draw the tissue approximately through the channel. Alternatively or additionally, a negative pressure may be provided at the remote of the channel in order to draw or pull the tissue approximately out of the probe. Alternatively or additionally, a positive pressure may be provided at the distal end of the channel in order to push tissue approximately through the channel

BRIEF DESCRIPTION OF THE DRAWINGS

Other objects and advantages of the present invention will be understood by reference to the following detailed description of the invention when considered in combination with the accompanying Figures, in which like reference numerals are used to identify like components throughout this disclosure.

DETAILED DESCRIPTION OF THE INVENTION

Figure 1A:
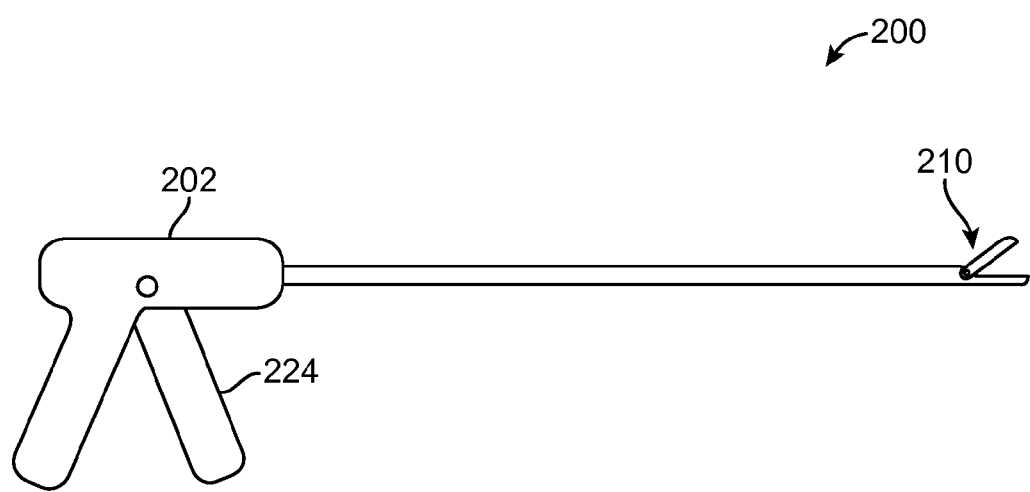
FIG. 1A is a view of a medical instrument corresponding to the invention.
Figure 1B:
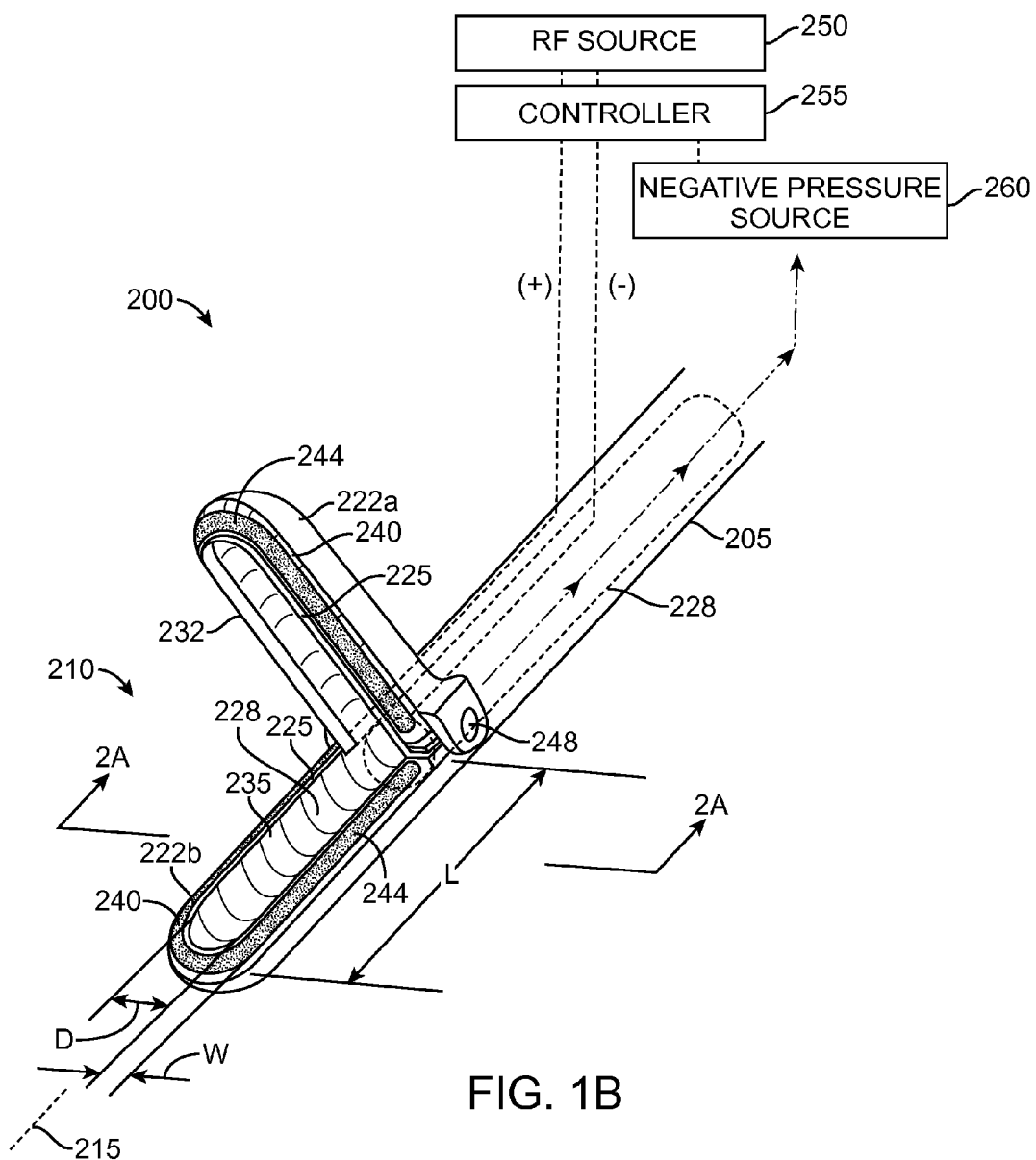
FIG. 1B is a perspective view of a working end of the instrument of FIG. 1A with first and second jaws having a cutting edge about a first perimeter and an energy delivery surface outward of the cutting edge for applying heat and pressure to engaged tissue.

Referring to FIGS. 1A-1B, a medical instrument 200 is shown with a handle 202 and elongated introducer or shaft member 205 that carries the working end 210 and is adapted for transecting and remodeling tissue. In one embodiment, the instrument is adapted for arthroscopy wherein the shaft member 205 extending along axis 215 can have a diameter ranging from 3 mm to 8 mm. The working end 210 comprises an openable-closeable jaw assembly with first (upper) jaw 222a and second (lower) jaw 222b that close and engage tissue about axis 215. The shaft member 205 can have a cylindrical or rectangular cross-section and can comprise a thin-wall tubular sleeve that extends from handle 202. In one embodiment, the handle 202 has a lever arm 224 that is adapted to actuate a translatable, reciprocating member that functions as a jaw-closing mechanism as is known in the art.

In one embodiment shown in FIG. 1B, jaw member 222a has a first or inner surface portion 225 extending around an interior tissue extraction channel 228 defined by the two jaws, wherein at least one tissue cutting element 232 is carried about a first surface portion 225. In this variation, the cutting element is a sharp blade edge 232 carried by the upper jaw 222a. The sharp blade edge 232 is configured for shearing tissue against the edge 235 of the extraction channel 228 in lower jaw 222b. In another variation, both jaws can carry sharp blade edges that shear against each other to transect tissue.

Figure 2A:
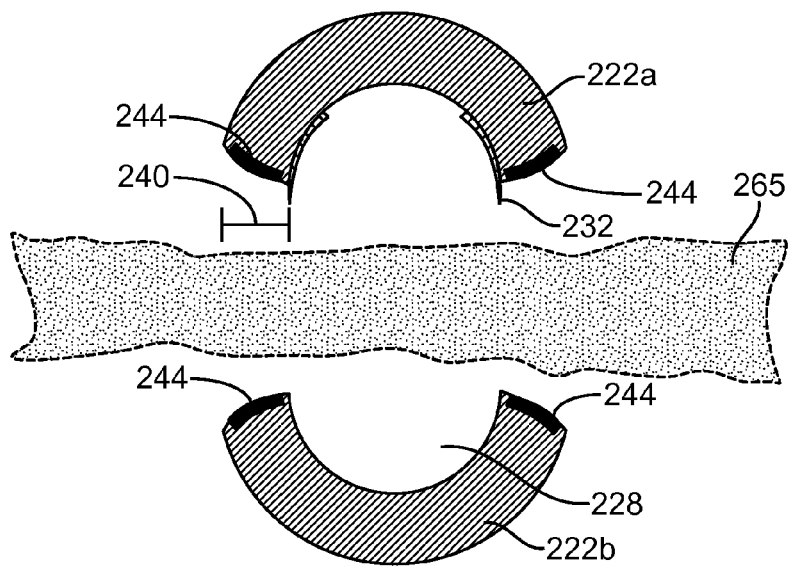
FIG. 2A is a sectional schematic view of the working end of FIG. 1 taken along line 2A-2A showing the first and second jaws being prepared to engage tissue in a method of using the working end of the invention.
Figure 2B:
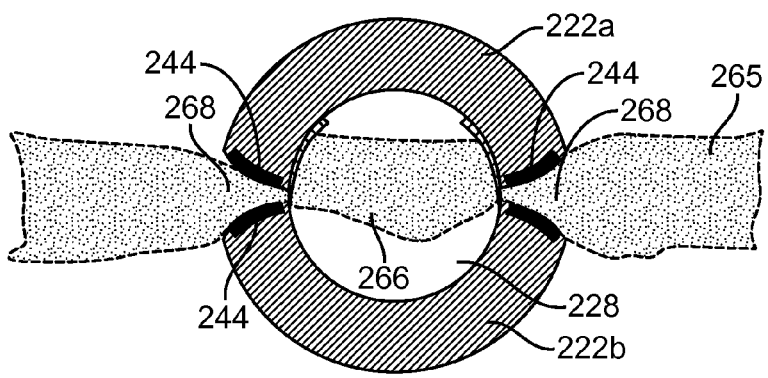
FIG. 2B is another sectional view of the working end of FIG. 2A showing the first and second jaws transecting tissue and applying heat and compression to remodel the remaining tissue edges outward of the transected tissue.
Figure 2C:
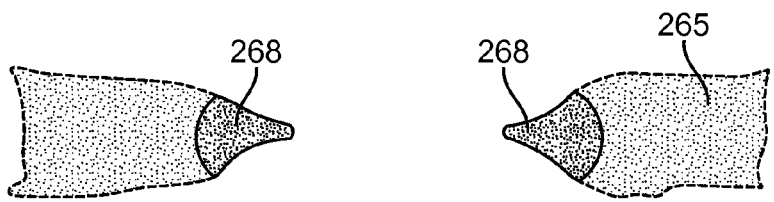
FIG. 2C is a sectional view of remodeled tissue edges following the application of heat and compression.

In the embodiment of FIGS. 1B and 2A-2B, each jaw has a second surface portion 240 outward of the blade edge 232 and in upper jaw 222a edge 235 in lower jaw 222b, where the second surface portion 240 is formed over a heat emitter 244 for applying thermal energy to engaged tissue for remodeling such tissue under pressure. The second surface portion 240 can have a gripping surface for gripping tissue, for example, a surface with fine ridges or an abrasive surface (not illustrated). In one variation, the second surface portions 240 in the opposing jaws are configured to define a tapered region that tapers toward the cut edges of the tissue as shown in FIGS. 2B-2C. By applying heat through the heat emitter 244, a tapered edge can be formed or "remodeled" into transected tissue margins 268 which can be beneficial in treatment of cartilage and other tissues, for example, any tissues which are formed at least partly of collagen and can be thermally denatured and effectively molded or remodeled.

In one variation as depicted in FIGS. 1B and 2A-2B, the heat emitters 244 can comprise PTCR (positive temperature coefficient of resistance) elements that are disposed on or within a jaw body. Suitable materials for forming the PTCT elements are described, for example, in U.S. Pat. Nos. 7,309, 849; 7,087,054; 7,955,331; 8,075,555; and 8,192, 428, the full disclosures of which are incorporated herein by reference. The PTCR elements 244 can be positioned within an insulated layer if the jaw body is a conductive material or can be embedded in a plastic or other insulative jaw body. The PTCR elements comprise constant temperature heaters in which electrical energy provided by an electrical source 250 and controller 255 resistively heats the PTCR material to a predetermined temperature level at which the material switches between electrically conductive and non-conductive. In FIG. 1B, it can be understood that positive and negative electrical leads extend to each PTCR element in the upper and lower jaws. The PTCR material can be configured to have a constant or switching temperature that is suited for remodeling collagenous tissue under pressure, such 55° C. or less, 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C. or 80° C. At such temperatures, collagen fibrils will denature, unwind and can be remodeled under pressure wherein thermal relaxation will result in a remodeled collagen shape.

Referring to FIG. 1B, the diameter or cross-section of the shaft 205 can be from about 3 mm to 8 mm. The diameter D of the extraction channel can range from about 2.5 mm to 7.5 mm. A typical device for use in arthroscopy has a diameter of about 5 mm. The width W of the second surface portion 240 can range from about 1 mm to 4 mm. The length L of the jaws can range from about 3 mm to 5 mm as in a type of 'punch' currently used in trimming cartilage, meniscus etc. or the jaws can be longer, for example 5 mm to 20 mm in length. In FIG. 1b, the jaws 222a and 222b are shown with the upper jaw pivoting around pin 248 but any type of jaw configuration is possible.

In FIG. 1B, it can be seen that a negative pressure source 260 communicates with the tissue extraction channel 228 which is configured for aspirating transected tissue proximally through the channel 228 in the instrument to a collection reservoir. Typically, the instrument working end 210 would be operated in a saline fluid environment, and in one variation the aspiration function can operate only when the jaws are closed. Alternatively, the aspiration mechanism can be manually turned ON when needed by the physician.

In another variation, the interior of the jaws can be configured with an electrode arrangement to provide for explosive vaporization of captured saline when the jaws are in the closed position to expel the transected tissue in the proximal direction, generally as disclosed in co-pending U.S. patent application Ser. No. 13/277,913, filed Oct. 20, 2011, titled TISSUE EXTRACTION DEVICES AND METHODS, now U.S. Pat. No. 8,512,326.

FIGS. 2A-2C show a method of using the working end of FIG. 1B to cut and remodel tissue. In FIG. 2A, a transverse sectional view of the jaws 222a and 222b can be seen in an open position preparing to engage tissue 265, which for example can be cartilage or meniscus. FIG. 2B depicts the jaws 222a and 222b closing on the tissue 265 with the sharp blade edge 232 cutting the tissue and capturing transected tissue 266 in the interior channel 228. At the same time, FIG. 2B illustrates heat being applied to the tissue margins 268 from the PTCR emitters 244 to remodel the engaged tissue. FIG. 2C shows the tissue margins 268 after heating and compression wherein the thermal remodeling can provide a tapered tissue margin which is needed in treatments of joint tissue.

Figure 3:
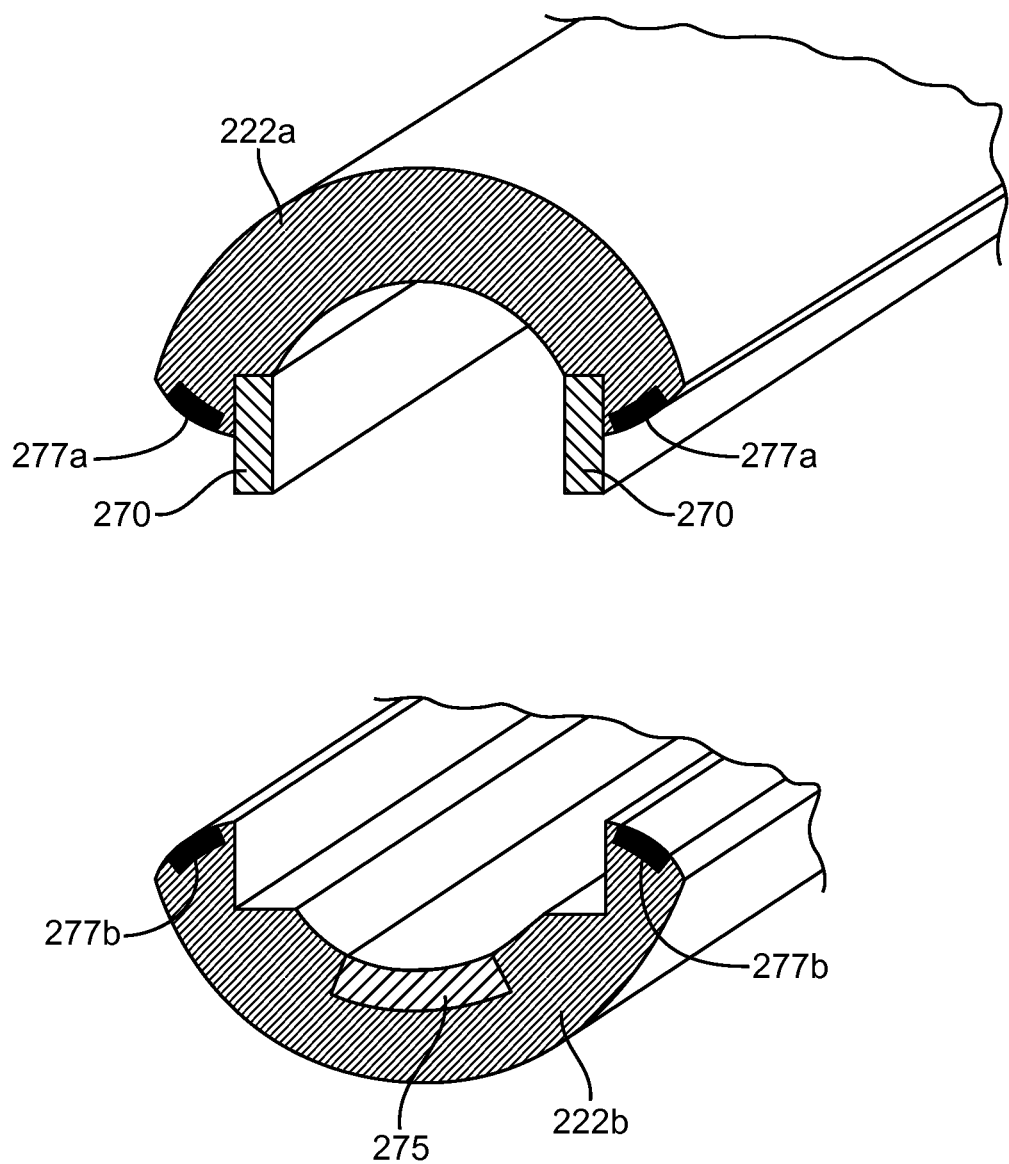
FIG. 3 is another variation of working end similar to that of FIG. 1 with an RF electrode cutting edge.

In another embodiment, referring to FIG. 3, the cutting edge can comprise an RF electrode 270 that creates a plasma for cutting tissue. In FIG. 3, the RF electrode 270 can cooperate with opposing polarity electrode 275 in the interior of the lower jaw. In this embodiment, the heat emitters 277a and 277b in the respective jaws 222a and 222b can comprise opposing polarity electrodes or PTCR elements as described previously.

In general, the device corresponding to the invention comprises an elongated probe with a working end 210 having openable-closeable first and second jaws wherein at least one jaw has a first surface portion carrying a tissue cutting element and a second surface portion outward of the first surface portion carrying a heat emitter configured for applying thermal energy for remodeling tissue, and not for cutting tissue. The independent cutting element can comprise a blade edge or at least one RF electrode.

In general, a method of treating joint tissue comprises providing an elongated probe with a working end having openable-closeable first and second jaws having a first inner tissue-cutting perimeter and a second outer tissue-remodeling perimeter, clamping tissue between the first and second jaws and cutting tissue engaged within the first perimeter and remodeling tissue engaged intermediate the second and first perimeters. The cutting step can be accomplished by a sharp edge at the first perimeter of at least one jaw or an RF electrode edge at the first perimeter of at least one jaw. The remodeling step is accomplished at least in part by heating tissue captured intermediate the second and first perimeters. The heating step can be provided by at least one of Joule heating and passive conductive heating. The method further comprises capturing cut and mobilized tissue within a channel within at least one jaw, and transporting tissue in the proximal direction within a channel extending through the elongated probe. Typically, the cut and mobilized tissue is transported under the influence of fluidic pressure, which can be negative pressure that pulls the tissue proximally and/or positive pressure that pushes the tissue proximally.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of treating tissue, comprising:
    clamping a selected tissue volume between a first jaw and a second jaw;
    cutting the tissue volume clamped between the jaws with a cutting element disposed on at least one of the first jaw and the second jaw; and
    remodeling the tissue volume clamped between the jaws with a remodeling element disposed on at least of the first jaw and the second one jaw.

2. The method of claim 1 the cutting element comprises a sharp edge at a first perimeter of the at least one jaw which cuts the tissue volume.

3. The method of claim 1 the cutting element comprises an RF electrode edge at a first perimeter of the at least one jaw which cuts the tissue volume.

4. The method of claim 1 wherein remodeling comprises heating tissue clamped between the jaws.

5. The method of claim 4 wherein said heating comprises Joule heating and/or passive conductive heating.

6. The method of claim 4 wherein said heating comprises passing RF current between first and second opposing polarity electrodes carried by the at least one jaw which cuts the tissue volume.

7. The method of claim 6 wherein the first and second opposing polarity electrodes are carried in the first and second jaws, respectively.

8. The method of claim 4 wherein said heating comprises passing current through a PTCR (positive temperature coefficient of resistance) material.

9. The method of claim 1 further comprising capturing cut tissue within a channel within at least one jaw of the first jaw and the second.

10. The method of claim 9 further comprising transporting the cut tissue in a proximal direction within the channel, wherein the channel extends through an elongated probe which carries the first jaw and the second jaw.

11. The method of claim 10 further comprising applying pressure to transport the cut tissue.

12. The method of claim 11 wherein the pressure is negative pressure that pulls the tissue proximally.

13. The method of claim 11 wherein the pressure is positive pressure that pushes the tissue proximally.

* * * * *